United States Patent

Pajotin et al.

Patent Number: 5,954,767
Date of Patent: Sep. 21, 1999

[54] CURVED PROSTHETIC MESH AND ITS METHOD OF MANUFACTURE

[75] Inventors: Docteur Philippe Pajotin, Cholet, France; John W. Coddaire, North Chelmsford; Fred D. Herzog, Westford, both of Mass.

[73] Assignee: C.R. Bard Inc., Murray Hill, N.J.

[21] Appl. No.: 08/686,151

[22] Filed: Jul. 24, 1996

Related U.S. Application Data

[63] Continuation of application No. 08/615,273, filed as application No. PCT/US94/10297, Sep. 13, 1994, abandoned.

[30] Foreign Application Priority Data

Sep. 13, 1993 [FR] France ................................. 93 10857

[51] Int. Cl.⁶ ........................................................ A61F 2/02
[52] U.S. Cl. ............................................. 623/11; 606/215
[58] Field of Search ...................... 623/11, 14; 606/213, 606/215

[56] References Cited

U.S. PATENT DOCUMENTS

| | | | |
|---|---|---|---|
| 2,671,444 | 3/1954 | Pease | 623/14 |
| 3,988,411 | 10/1976 | Capozza | 264/184 |
| 4,403,604 | 9/1983 | Wilkinson . | |
| 4,441,215 | 4/1984 | Kaster | 623/1 |
| 4,573,999 | 3/1986 | Netto | 623/11 |
| 4,693,720 | 9/1987 | Scharnberg | 623/11 |
| 4,728,328 | 3/1988 | Hughes | 623/12 |
| 4,841,948 | 6/1989 | Bauer | 623/11 |
| 5,146,933 | 9/1992 | Boyd | 623/11 |
| 5,258,000 | 11/1993 | Gianturco | 606/215 |
| 5,356,432 | 10/1994 | Rutkow et al. | 623/11 |
| 5,383,477 | 1/1995 | DeMatteis | 606/213 |
| 5,593,441 | 1/1997 | Lichtenstein et al. . | |
| 5,695,525 | 12/1997 | Mulhauser et al. . | |
| 5,725,577 | 3/1998 | Saxon . | |
| 5,743,917 | 4/1998 | Saxon . | |
| 5,766,246 | 6/1998 | Mulhauser et al. . | |

FOREIGN PATENT DOCUMENTS

| | | |
|---|---|---|
| 593 267 | 1/1988 | Australia . |
| 2 682 284 A1 | 4/1993 | France . |
| 892 663 | of 1953 | Germany . |
| 40 13 447 C1 | 2/1992 | Germany . |
| 92 12 261 | 11/1993 | Germany . |
| 2 226 762 | 11/1990 | United Kingdom . |
| WO 92/13500 | 8/1992 | WIPO . |

*Primary Examiner*—Michael J. Milano
*Attorney, Agent, or Firm*—Wolf, Greenfield & Sacks, P.C.

[57] ABSTRACT

A prothesis is provided for repairing a defect in a muscle or tissue wall. The prothesis has a preformed shape that conforms to the wall to facilitate placement and minimize shifting of the prosthesis when positioned on the wall. The prosthesis may include a body formed of a sheet of surgical mesh fabric having a flexible inner portion surrounded by a stiffer periphery that is capable of resuming the preformed shape after being temporarily deformed to allow for implantation. The body may include a tapered end to facilitate insertion of the prothesis between the parietal peritoneum and the abdominopelvic wall during hernia repairs. The body may also include a curved end to permit repositioning of the bladder after implantation. In one embodiment, the prothesis includes a conical portion at the tapered end and a spherical portion at the curved end. The body may also include a permanent depression on a surface that receives the iliac vessels when the prothesis is positioned on the wall to repair an inguinal hernia.

41 Claims, 3 Drawing Sheets

CURVED PROSTHETIC MESH AND ITS METHOD OF MANUFACTURE

This application is a continuation of application Ser. No. 08/615,273 filed Mar. 13, 1996, abandoned which is a 371 of PCT/US94/10297, filed Sep. 13, 1994.

BACKGROUND OF THE INVENTION

1. Field of the Invention

The present invention relates to prosthetic meshes and their methods of manufacture.

2. Description of the Related Art

The prior art includes a prosthetic mesh made of an implantable, non-resorbable, flexible material, designed to be implanted for the parietal repair of hernias and eventrations of the abdominal wall. These meshes, which are usually made of implantable polypropylene, preferably have tight mesh openings and are obtained by knitting, welding or weaving. They are supplied to surgeons pre-cut, in the form of a flat element. However, this flat element must be applied to a concave surface by the surgeon. As a result of the difference in conformation, the mesh is difficult to put into position, especially since one of its relatively broad margins has to be slipped between the parietal peritoneum and the abdominopelvic wall. Moreover, as it is being put in place, the mesh folds or wrinkles and is hard to keep in place at the point where many surgeons prefer to attach it. Its inner margin corresponding to the other small side must be slipped between the bladder and the abdominopelvic wall. A straight margin is poorly suited for insertion of the internal edge.

SUMMARY

The invention palliates these disadvantages by means of a mesh which is easier to put in place and which, once in position, has virtually no tendency to shift, without the need for any additional intervention such as fixation, thereby making it possible to reinforce all the weak points of the inguinofemoral region, resulting in a much lower failure rate than heretofore.

According to the invention, the mesh assumes a curved shape of itself.

Due to this natural curvature which is imparted to it during fabrication and which can match the concavity on which it is to be placed, on being put into place by the surgeon the mesh conforms to the anatomic shapes, and it has no tendency to shift because it is not subjected to strain due to its deformation. By preference, the mesh, while being capable of the temporary deformation necessary for it to be put in place, should have a sufficient tendency to resume its initial curved shape, without deviating therefrom, so that it does not fold or wrinkle under the pressure of the viscera. The preferred mesh resumes its approximate original shape after a single temporary deformation. To obtain this effect more easily, it is desirable for the margins of the mesh to be more rigid than the rest of the mesh, for example by fusing of the material marginally over a width of at least 5 mm. The margins are preferably smooth, to keep the mesh from catching as it is being positioned.

To facilitate insertion, it is preferred that the mesh have, not an external side, but a roughly tapered end by which it can be slipped more easily between the parietal peritoneum and the abdominopelvic wall. It is also preferred that its inner margin, the farthest from that end, be incurvated, especially in its outer portion, roughly according to a circle permitting the repositioning of the bladder after the mesh has been put in place.

For optimum fitting of the mesh to the areas requiring reinforcement, the mesh can have a double convexity in two perpendicular planes.

According to one embodiment, this mesh is composed of a part in the form of a spherical cap extending from the inner margin to beyond the location where the strongest reinforcement is desired, prolonged by a conical part which, at its end, defines the outer tip. The radius of the spherical part can be between 80 and 120 mm. The largest dimension of the mesh can be between 120 and 150 mm, while the dimension perpendicular to this largest dimension can be between 70 and 100 mm.

In order for the mesh to fit optimally into the pelvic area, a rounded edge is provided between the spherical cap and the cone on one hand, and a lower part with a large radius of curvature, which has a depression near its center. This depression is designed to be placed opposite the external iliac vessels, while the rounded edge is designed to be placed within the axis of the inguinal ligament.

A further object of the invention is a method of manufacture of a mesh according to the invention, which consists in placing a flat piece of an implantable, non-resorbable, flexible material in a curved template and bringing this piece to a sufficient temperature for a sufficient period of time so that it retains a curved shape, even after cooling, and upon removal from the template.

A final object of the invention is a package for a mesh, which comprises a body in which a cover nests, characterized in that the upper surface of the bottom of the body is derived from a template which, together with a concave part of the same shape provided on the lower surface of the cover, defines a receptacle for the curved mesh.

In the attached drawings, provided solely as examples:

DETAILED DESCRIPTION

Figure 1:
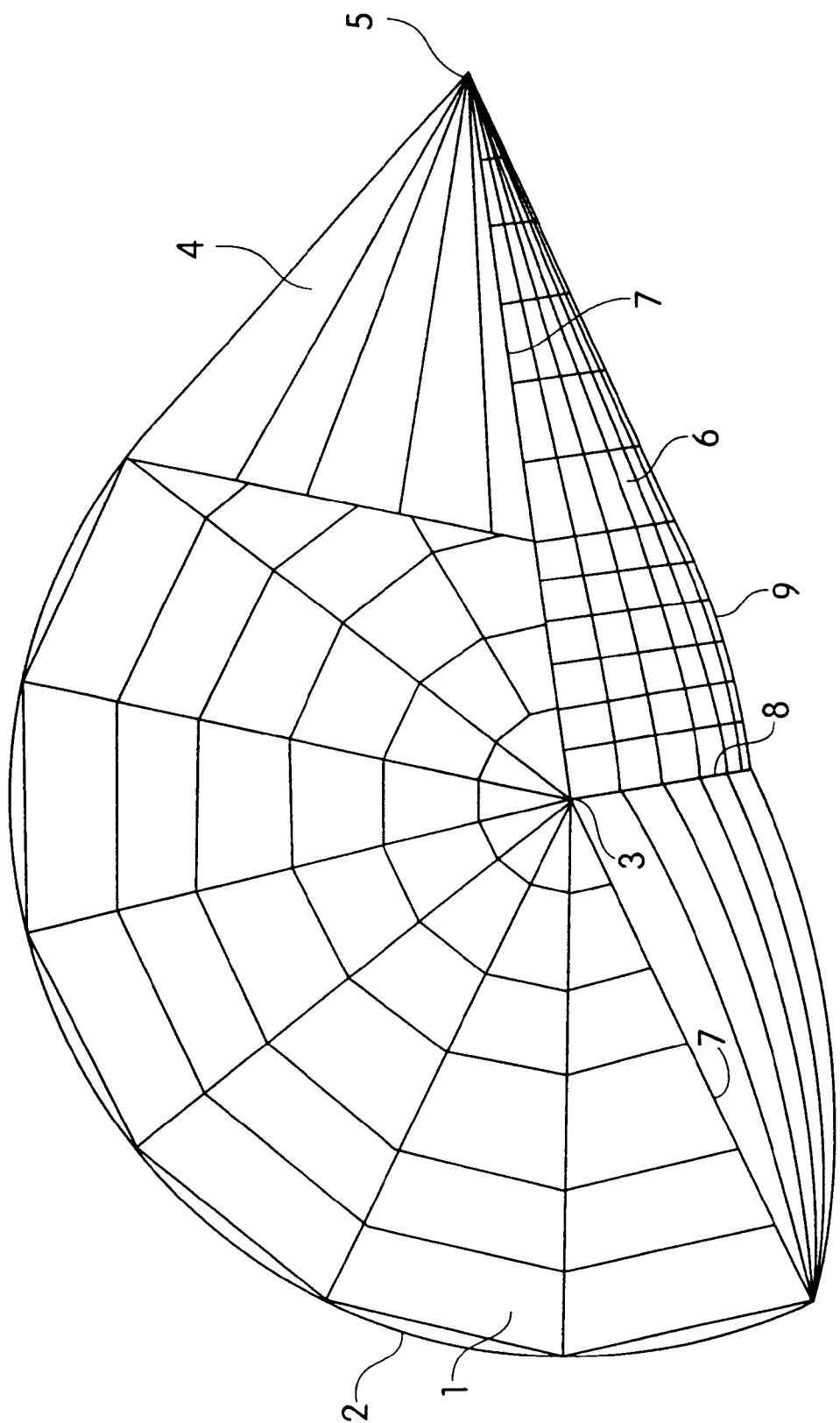
FIG. 1 is a plan view of the mesh according to the invention.
Figure 2:
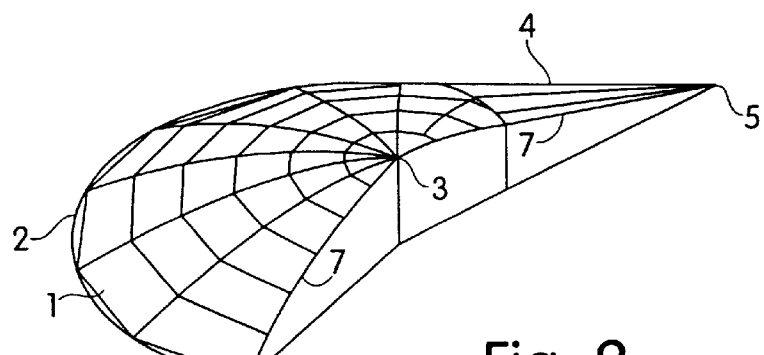
FIG. 2 is a perspective view, partially cut away, of the mesh according to the invention.

The mesh according to the invention is made of knitted polypropylene (Marlex) cloth; for purposes of clarity, the mesh openings are shown in the drawing as larger than they really are.

The prosthetic mesh is comprised of a curved inner portion forming an open-ended cavity surrounded by a peripheral edge of the mesh that includes a first/inner margin 2 and a second/bottom margin 9. The inner portion includes a part 1 in the form of a spherical cap extending from the rounded inner margin 2 of the peripheral edge to beyond the location 3 where the strongest reinforcement is desired. This spherical cap 1 is prolonged by a conical part 4 which defines at its end the outer tip 5. The radius of spherical part 1 is 100 mm, the largest dimension of the mesh from inner margin 2 to the tip 5 is 130 mm, while the dimension perpendicular to this largest dimension is 85 mm. The inner portion also includes a lower part 6 is connected both to the spherical cap 1 and to the cone 4 by a rounded edge 7, and a depression 8 is provided beginning at the bottom margin 9 of the peripheral edge along the lower part, near the median portion. The spherical cap 1 and the conical part 4 form a first curved surface and the lower part 6 forms a second curved surface on opposite sides of the rounded edge 7.

All the margins of the mesh are smooth and are made more rigid than the rest by fusing the material marginally over a width of 3 mm.

Figure 3:
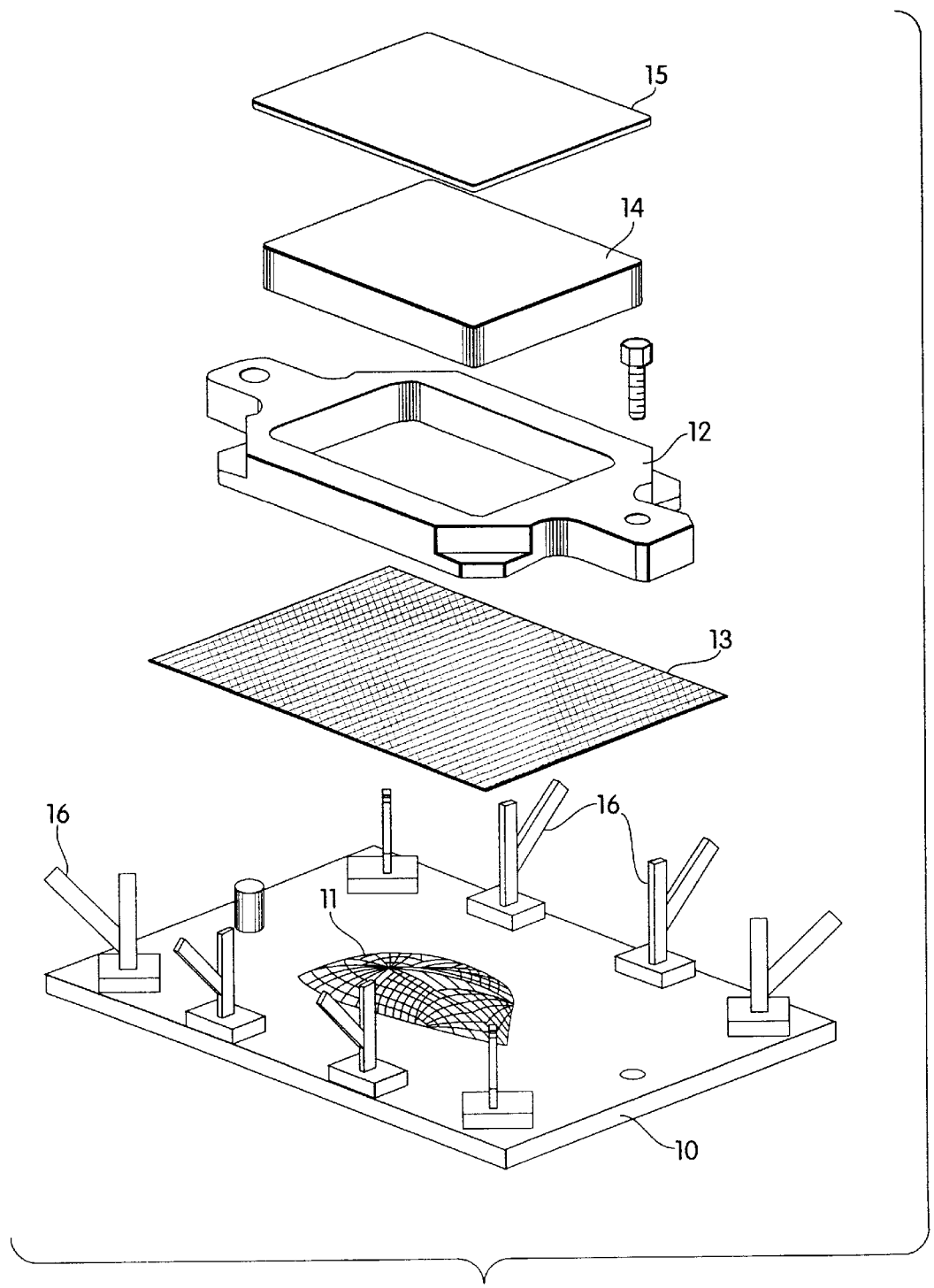
FIG. 3 is an exploded view depicting the method of manufacture of the mesh according to the invention.

In FIG. 3, a template consists of a supporting base 10, from the surface of which is derived a template per se 11 in the shape of the mesh to be obtained, and an aluminum frame 12 designed to clamp the margins of a flat piece of mesh 13 when it is placed on the template 11 after the retaining tabs 16 have been folded down. A silicone frame 14 with a form similar to the template 11 recessed into its inner surface can then be placed on the mesh 13 and held there by an aluminum cover plate 15. Once the flat piece 13 of mesh has been secured in this fashion, it is heated in the template to a temperature of 150° C. for one hour. The template is cooled and the mesh, now curved, is removed.

Figure 4:
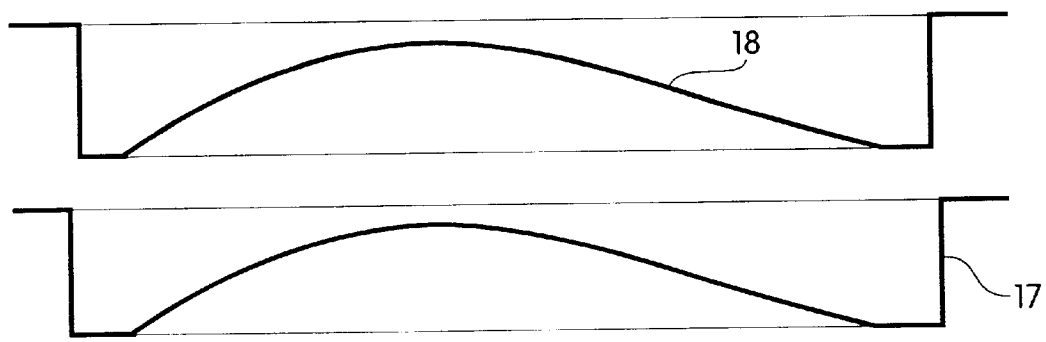
FIG. 4 depicts a package for the mesh.

FIG. 4 depicts a package for the curved mesh. This package consists of a body 17, the upper surface of whose bottom is inwardly convex in the shape of the mesh which it is to hold, and a cover 18 which is inwardly concave in this same shape. When the cover 18 is placed in the body 17, a curved receptacle is defined and the curved mesh is thus held between these two parts in the desired shape.

What is claimed is:

1. An implantable prosthesis for repairing a defect in a muscle or tissue wall, the prothesis comprising:

a sheet of surgical prosthetic material including an inner portion and a peripheral edge surrounding the inner portion, the inner portion having a preformed contoured shape curved in three dimensions that forms a cavity with an open end surrounded by the peripheral edge, the inner portion being constructed and arranged to conform to the wall and to minimize shifting of the prosthesis when positioned on the wall, the peripheral edge including at least first and second opposed margins, the first margin having a first curvature and the second margin having a second curvature which is less than the first curvature.

2. The prosthesis recited in claim 1, wherein the first margin includes a semicircular segment.

3. The prosthesis recited in claim 1, wherein the first margin includes an arcuate segment and a straight segment extending from an end of the arcuate segment.

4. The prosthesis recited in claim 1, wherein the second margin includes a permanent depression intermediate each end of the second margin, the depression constructed and arranged to be placed proximate the iliac vessels when the prosthesis is positioned on the wall to repair an inguinal hernia.

5. The prosthesis recited in claim 1, wherein the periphery is generally D-shaped.

6. The prosthesis recited in claim 1, wherein the second margin is slightly curved.

7. The prosthesis recited in claim 1, wherein the second margin includes:

first and second adjacent curved segments; and a depression disposed between the first and second segments that is adapted to be placed proximate the iliac vessels when the prosthesis is positioned on the wall to repair an inguinal hernia.

8. The prosthesis recited in claim 1, wherein the peripheral edge is stiffer than the inner portion so that the inner portion can regain the contoured shape after being deformed.

9. The prosthesis recited in claim 1, wherein the sheet of prosthetic material includes surgical mesh.

10. A prosthesis for repairing a defect in a muscle or tissue wall, the prothesis comprising:

a body including a sheet of prosthetic mesh fabric having a plurality of openings therein, the body having a preformed three dimensional shape constructed and arranged to conform to the wall, the body including a preformed permanent depression on a surface thereof that is constructed and arranged to receive the iliac vessels when the prosthesis is positioned on the wall to repair an inguinal hernia.

11. The prosthesis recited in claim 10, wherein the body has a peripheral edge and the depression extends inwardly from the peripheral edge.

12. The prosthesis recited in claim 11, wherein the body includes first and second curved surfaces, the second curved surface having a steeper incline than the first curved surface.

13. The prosthesis recited in claim 12, wherein the depression is disposed on the second curved surface.

14. The prosthesis recited in claim 12, wherein the first curved surface includes a first portion having a generally spherical shape.

15. The prosthesis recited in claim 14, wherein the first portion of the first curved surface has a radius between approximately 80 mm and approximately 120 mm.

16. The prosthesis recited in claim 12, wherein the first and second curved surfaces respectively have first and second surface areas, the first surface area being greater than the second surface area.

17. The prosthesis recited in claim 16, wherein the first curved surface further includes a second portion adjacent the first portion, the second portion having a generally conical shape extending away from the first portion.

18. The prosthesis recited in claim 11, wherein the body includes an apex and the depression extends from the apex to the peripheral edge.

19. An implantable prosthesis for repairing a defect in a muscle or tissue wall, the wall having an anatomical shape, the prothesis comprising:

a body of resilient surgical mesh fabric having a plurality of openings therein, the body including an inner portion and a peripheral edge surrounding the inner portion, the inner portion having a preformed shape curved in three dimensions that is adapted to conform to the anatomical shape of the wall, the preformed shape having a spherical portion and a conical portion extending from the spherical portion, the peripheral edge being stiffer than the inner portion so that the body can regain the preformed curved shape after being deformed.

20. The prosthesis recited in claim 19, wherein the inner portion includes first and second curved surfaces, the first curved surface adjoining the second curved surface along a rounded edge therebetween, the second curved surface having a steeper incline than the first curved surface.

21. The prosthesis recited in claim 20, wherein the inner portion includes an apex and the rounded edge extends through the apex.

22. The prosthesis recited in claim 20, wherein the first curved surface includes a curved portion having a radius between about 80 mm and about 120 mm.

23. The prosthesis recited in claim 20, wherein the first curved surface includes the spherical portion and the conical portion extending from the spherical portion.

24. The prosthesis recited in claim 20, further comprising a permanent depression disposed in the second curved surface, the depression adapted to be placed proximate the iliac vessels when the prosthesis is positioned on the wall to repair an inguinal hernia.

25. An implantable prosthesis for repairing a defect in a muscle or tissue wall, the prothesis comprising:

a body of prosthetic material having a preformed shape constructed and arranged to conform to the wall, the preformed shape of the body including first and second curved surfaces, the second curved surface having a steeper incline than the first curved surface.

26. The prosthesis recited in claim 25, wherein the body includes a sheet of material having an inner portion and a peripheral edge surrounding the inner portion, the first curved surface adjoining the second curved surface along a rounded edge therebetween, the rounded edge extending across the inner portion from a first location on the peripheral edge to a second location on the peripheral edge.

27. The prosthesis as recited in claim 25, wherein the body has a permanent depression formed in the second curved surface, the depression adapted to be placed proximate the iliac vessels when the prosthesis is positioned on the wall to repair an inguinal hernia.

28. The prosthesis as recited in claim 25, wherein the body includes an inner portion surrounded by a peripheral edge, the peripheral edge being more rigid than the inner portion so that the body can regain the preformed shape after being deformed.

29. The prosthesis recited in claim 25, wherein the first curved surface includes a generally convex portion having a predetermined radius.

30. The prosthesis recited in claim 29, wherein the predetermined radius is between approximately 80 mm and approximately 120 mm.

31. A prosthesis for repairing a defect in a muscle or tissue wall, the prothesis comprising:

a preformed surgical mesh having a generally curved shape, the mesh having adjacent first and second curved surfaces, the first curved surface including a spherical portion and a conical portion extending from the spherical portion, the second curved surface having a steeper incline than the first surface;

a rounded edge disposed between the first and second curved surfaces that is adapted to be placed within the axis of the inguinal ligament when the prosthesis is positioned on the wall to repair an inguinal hernia; and a permanent depression disposed in the second curved surface that is adapted to be placed opposite the iliac vessels when the prosthesis is positioned on the wall.

32. The prosthesis recited in claim 31, wherein the mesh has a maximum dimension between approximately 120 mm and approximately 150 mm and a dimension perpendicular to the maximum dimension between approximately 70 mm and approximately 100 mm.

33. A prosthesis for repairing a defect in a muscle or tissue wall having an anatomical shape, the prothesis comprising:

a sheet of surgical mesh having a preformed shape adapted to conform to the anatomical shape of the wall, the preformed shape of the mesh including a generally convex outer surface, and a generally concave inner surface, a tapered end portion and a curved end portion.

34. The prosthesis recited in claim 33, wherein the mesh includes an inner portion surrounded by a peripheral edge, the inner surface of the inner portion defining a cavity having an open end surrounded by the peripheral edge of the mesh.

35. The prosthesis recited in claim 33, wherein the mesh includes an inner portion and a peripheral edge surrounding the inner portion, the peripheral edge being more rigid than the inner portion so that the mesh can regain the preformed shape after being deformed.

36. The prosthesis recited in claim 35, wherein the peripheral edge is smooth to prevent the mesh from catching when being positioned on the wall.

37. The prosthesis recited in claim 33, wherein the mesh includes a spherical component at the curved end portion.

38. The prosthesis recited in claim 33, wherein the mesh includes a triangular component at the tapered end portion.

39. The prosthesis recited in claim 33, wherein the mesh has a generally D-shaped peripheral edge.

40. The prosthesis recited in claim 25, wherein the first curved surface includes a spherical portion and a conical portion extending from the spherical portion.

41. The prosthesis recited in claim 40, wherein the second curved surface adjoins the first curved surface along a rounded edge therebetween.

\* \* \* \* \*